United States Patent
Bhullar et al.

(10) Patent No.: US 6,755,949 B1
(45) Date of Patent: Jun. 29, 2004

(54) BIOSENSOR

(75) Inventors: Raghbir S. Bhullar, Indianapolis, IN (US); Christopher D. Wilsey, Carmel, IN (US); John T. Austera, Indianapolis, IN (US)

(73) Assignee: Roche Diagnostics Corporation, Indianapolis, IN (US)

(*) Notice: Subject to any disclaimer, the term of this patent is extended or adjusted under 35 U.S.C. 154(b) by 37 days.

(21) Appl. No.: 09/974,434

(22) Filed: Oct. 9, 2001

(51) Int. Cl.[7] .................. G01N 27/327; G01N 27/333
(52) U.S. Cl. .................. 204/409; 204/416; 204/403.01; 422/50
(58) Field of Search .................. 204/403.01, 416, 204/409; 422/99, 50, 58, 55, 70, 82.01–82.03

(56) References Cited

U.S. PATENT DOCUMENTS

| | | | |
|---|---|---|---|
| 4,233,029 A | 11/1980 | Columbus | 23/230 |
| 4,271,119 A | 6/1981 | Columbus | 422/50 |
| 4,302,313 A | 11/1981 | Columbus | 204/195 |
| 4,323,536 A | 4/1982 | Columbus | 422/56 |
| 4,618,476 A | 10/1986 | Columbus | 422/100 |
| 4,948,961 A | 8/1990 | Hillman et al. | 250/252.1 |
| 4,963,814 A | 10/1990 | Parks et al. | 323/274 |
| 4,999,582 A | 3/1991 | Parks et al. | 324/438 |

(List continued on next page.)

FOREIGN PATENT DOCUMENTS

| | | | |
|---|---|---|---|
| EP | 0 289 269 | 11/1988 | G01N/27/40 |
| EP | 0 348 006 A2 | 12/1989 | B01L/3/00 |
| EP | 1 098 000 A2 | 5/2001 | C12Q/1/00 |
| EP | 1 113 263 A2 | 7/2001 | G01N/27/327 |
| EP | 1 120 164 A2 | 8/2001 | B01L/3/00 |
| EP | 1 195 441 A1 | 4/2002 | C12Q/1/00 |
| EP | 1 203 956 A2 | 5/2002 | G01N/33/487 |
| EP | 1 211 321 A1 | 6/2002 | C12Q/1/00 |
| WO | WO 98 43739 | 10/1998 | B01L/3/00 |
| WO | WO 00/73778 | 12/2000 | G01N/27/327 |
| WO | WO 00/73785 | 12/2000 | G01N/33/00 |

OTHER PUBLICATIONS

LPKF MicrolineLaser II, LPKF Laser & Electronics AG; LPKF; Art.–Nr. 107645–2 (01/00) (2pp.).
Microline Solutions, LPKF Laser & Electronics AG; LPKF; Art.–Nr. 107658–1 (01/00) (4pp.).
FastTake™ Compact Blood Glucose Monitoring System, Owner's Booklet, Lifescan Inc. 1997 (45 pp).

*Primary Examiner*—Alex Noguerola
(74) *Attorney, Agent, or Firm*—Jill L. Woodburn (57) ABSTRACT

A biosensor is provided in accordance with the present invention. The biosensor includes a substrate and a cover extending across at least a portion of the substrate. The cover includes a first surface facing the substrate and a second surface. At least a portion of the first surface is removed to define a capillary channel. The capillary channel has a surface energy ranging from about 60 mN/m to about 72 mN/m.

25 Claims, 8 Drawing Sheets

U.S. PATENT DOCUMENTS

| | | |
|---|---|---|
| 4,999,632 A | 3/1991 | Parks .......................... 324/167 |
| 5,119,116 A | 6/1992 | Yu .............................. 346/140 |
| 5,243,516 A | 9/1993 | White ................... 364/413.07 |
| 5,300,779 A | 4/1994 | Hillman et al. ............. 250/341 |
| 5,352,351 A | 10/1994 | White et al. ................ 204/406 |
| 5,366,609 A | 11/1994 | White et al. ................ 204/403 |
| 5,405,511 A | 4/1995 | White et al. ............. 204/153.1 |
| 5,413,690 A | 5/1995 | Kost et al. .................. 204/403 |
| 5,418,142 A | 5/1995 | Kiser et al. ................... 435/14 |
| 5,438,271 A | 8/1995 | White et al. ................ 324/444 |
| 5,520,244 A | 5/1996 | Mundinger et al. .... 165/104.33 |
| 5,620,863 A | 4/1997 | Tomasco et al. .............. 435/14 |
| 5,637,458 A | 6/1997 | Frankel et al. ................. 435/6 |
| 5,658,444 A | 8/1997 | Black et al. ................ 204/415 |
| 5,753,452 A | 5/1998 | Smith .......................... 435/14 |
| 5,762,770 A | 6/1998 | Pritchard et al. ........... 204/403 |
| 5,798,031 A | 8/1998 | Charlton et al. ............ 204/403 |
| 5,837,115 A | 11/1998 | Austin et al. ............... 204/450 |
| 5,952,173 A * | 9/1999 | Hansmann et al. ............ 435/6 |
| 5,997,817 A | 12/1999 | Crismore et al. ............. 422/58 |
| 6,019,944 A | 2/2000 | Buechler ...................... 422/58 |
| 6,042,709 A | 3/2000 | Parce et al. .................. 204/453 |
| 6,048,498 A | 4/2000 | Kennedy ..................... 422/99 |
| 6,083,761 A | 7/2000 | Kedar et al. ................ 436/178 |
| 6,156,273 A | 12/2000 | Regnier et al. ............... 422/70 |
| 6,180,065 B1 | 1/2001 | Homola ..................... 422/102 |
| 6,251,343 B1 | 6/2001 | Dubrow et al. ............. 422/102 |
| 6,270,641 B1 | 8/2001 | Griffiths et al. ............. 204/451 |
| 6,271,040 B1 * | 8/2001 | Buechler .................... 436/170 |

* cited by examiner

BIOSENSOR

FIELD OF THE INVENTION

The present invention is directed to physical structures and methods for controlling the flow of small volumes of liquids through a biosensor. More particularly, the present invention is directed to such physical structures that define a capillary channel and microstructures.

BACKGROUND AND SUMMARY OF THE INVENTION

Electrochemical biosensors are known. They have been used to determine the concentration of various analytes from biological samples, particularly from blood. Electrochemical biosensors are described in U.S. Pat. Nos. 5,413,690; 5,762,770; 5,798,031; and 5,997,817 the disclosure of each of which is expressly incorporated herein by reference.

According to the present invention a biosensor is provided. The biosensor comprises a substrate and a cover extending across at least a portion of the substrate. The cover includes a first surface facing the substrate and a second surface. At least a portion of the first surface is removed to define a capillary channel. The capillary channel has a surface energy ranging from about 60 mN/m to about 72 mN/m.

According to another aspect of the invention a biosensor is provided. That biosensor comprises a capillary path defined between a substrate and a cover and at least one microstructure positioned in the capillary path. The at least one microstructure includes a fixed end coupled to either the substrate or the cover and an opposite free end, wherein the free end is metallic.

According to still another aspect of the present invention a biosensor is provided. The biosensor comprises a substrate, electrodes positioned on the substrate, a cover extending across at least a portion of the substrate to define a capillary path, and at least one microstructure positioned in the capillary path. The at least one microstructure includes a fixed end coupled to the cover and an opposite free end, wherein the free end is metallic.

According to still another aspect of the invention a method of forming biosensor is provided. The method comprises the steps of providing a substrate, a reagent for the measurement of at least one analyte, and a cover, the cover including a first surface, exposing the cover to at least one pulse of light of sufficient to ablate the first surface in a predetermined pattern creating a channel, cleaning the first surface of the cover so that the surface energy of the channel ranges from about 60 mN/m to about 72 mN/m, and placing the first surface of the cover upon the substrate to define a capillary path and the reagent is positioned in the capillary path.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

The present invention relates to a biosensor and method of manufacturing a biosensor that is formed to provide a well-controlled fluid flow and simultaneously reduce the volume of liquid sample required for testing. Biosensors can take the form of any number of diagnostic biosensors including, for example, electrochemical and photometric biosensors. Aspects of the invention are presented in FIGS. 1–11, which are not drawn to scale and wherein like components in the several views are numbered alike.

A biosensor 10 for testing for biologically significant analytes of an applied biological fluid is shown in FIGS. 1–5. The term analyte, as used herein, refers to the molecule or compound to be quantitatively determined. Non-limiting examples of analytes include carbohydrates, proteins, such as hormones and other secreted proteins, enzymes, and cell surface proteins; glycoproteins; peptides; small molecules; polysaccharides; antibodies (including monoclonal or polyclonal Ab); nucleic acids; drugs; toxins; viruses of virus particles; portions of a cell wall; and other compounds processing epitopes. The analyte of interest preferably comprises glucose.

Biosensor 10 has an electrode-support substrate 12, an electrical conductor 14 positioned on the substrate 12 that is disrupted to define electrodes 16, 18, and a cover substrate 20 positioned on substrate 12. Biosensor 10 is in the form of a disposable test strip. It is appreciated however, that biosensor 10 can assume any number of forms and shapes in accordance with this disclosure. Biosensor 10 is preferably produced from rolls of material however, it is understood that biosensor 10 can be constructed from individual sheets in accordance with this disclosure. Thus, when biosensors 10 are produced from rolls, the selection of materials necessitates the use of materials that are sufficiently flexible for roll processing, but which are still rigid enough to give a useful stiffness to finished biosensor 10.

Figure 1:
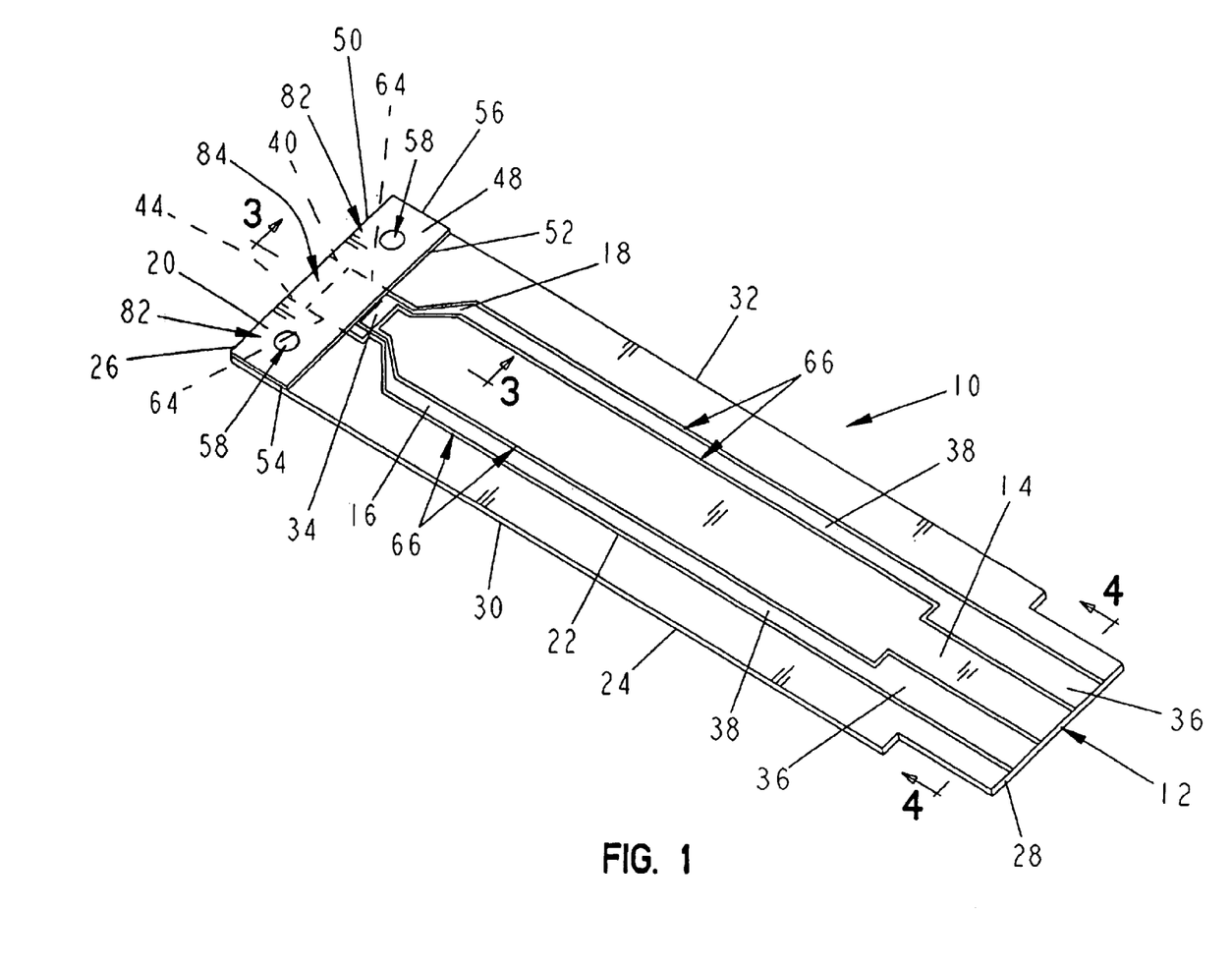
FIG. 1 is a perspective view of a biosensor in accordance with the present invention.

Referring to FIG. 1, the electrode-support substrate 12 includes a first surface 22 and a second surface 24. In addition, substrate 12 has opposite first and second ends 26, 28 and opposite edges 30, 32 extending between the first and second ends 26, 28. Substrate 12 is generally rectangular in shape, it is appreciated however, that support 12 may be formed in a variety of shapes and sizes in accordance with this disclosure. Substrate 12 may be constructed from a wide variety of insulative materials. Non-limiting examples of insulative materials that provide desirable electrical and structural properties include glass, ceramics, vinyl polymers, polyimides, polyesters, and styrenics. Preferably, substrate 12 is a flexible polymer, such as a polyester or polyimide. A non-limiting example of a suitable material is 5 mil thick KALADEX®, a polyethylene naphthalate film commercially available from E. I. DuPont de Nemours, Wilmington, Del., which is coated with gold by: ROWO Coatings, Herbolzheim, Germany.

Electrodes 16, 18 are created or isolated from conductor 14 on first surface 22 of electrode-support substrate 12. Electrodes 16, 18 are isolated from conductor 14 by gaps 66. See FIG. 4. It is also appreciated that electrodes 16, 18 can be formed, from multiple layers of same or different electrically conductive materials. Non-limiting examples of a suitable electrical conductor 14 include aluminum, carbon (such as graphite), cobalt, copper, gallium, gold, indium, iridium, iron, lead,: magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, electrical conductor 14 is selected from the following materials: gold, platinum, LA palladium, iridium, or alloys of these metals, since such noble metals and their alloys are unreactive in biological systems. Most preferably, electrical conductor 14 is gold.

Electrodes 16, 18 are isolated from the rest of the electrical conductor 14 by laser ablation. Techniques for forming electrodes on a surface using laser ablation are known. See, for example, U.S. patent application Ser. No. 09/411,940, titled "Laser Defined Features for Patterned Laminates and Electrodes", the disclosure of which is expressly incorporated herein by reference. Preferably, electrodes 16, 18 are created by removing the electrical conductor 14 from an area extending around the electrodes to form a gap of exposed support substrate 12. Therefore, electrodes 16, 18 are isolated from the rest of the electrically-conductive material on substrate 12 by a gap having a width of about 25 µm to about 500 µm preferably the gap has a width of about 100 µm to about 200 µm. Alternatively, it is appreciated that electrodes 16, 18 may be created by laser ablation alone on substrate 12. It is appreciated that while laser ablation is the preferred method for forming electrodes 16, 18 given its precision and sensitivity, other techniques such as lamination, screen-printing, photolithography, or contact printing may be used in accordance with this disclosure.

Figures 2A, 2B, 2C:
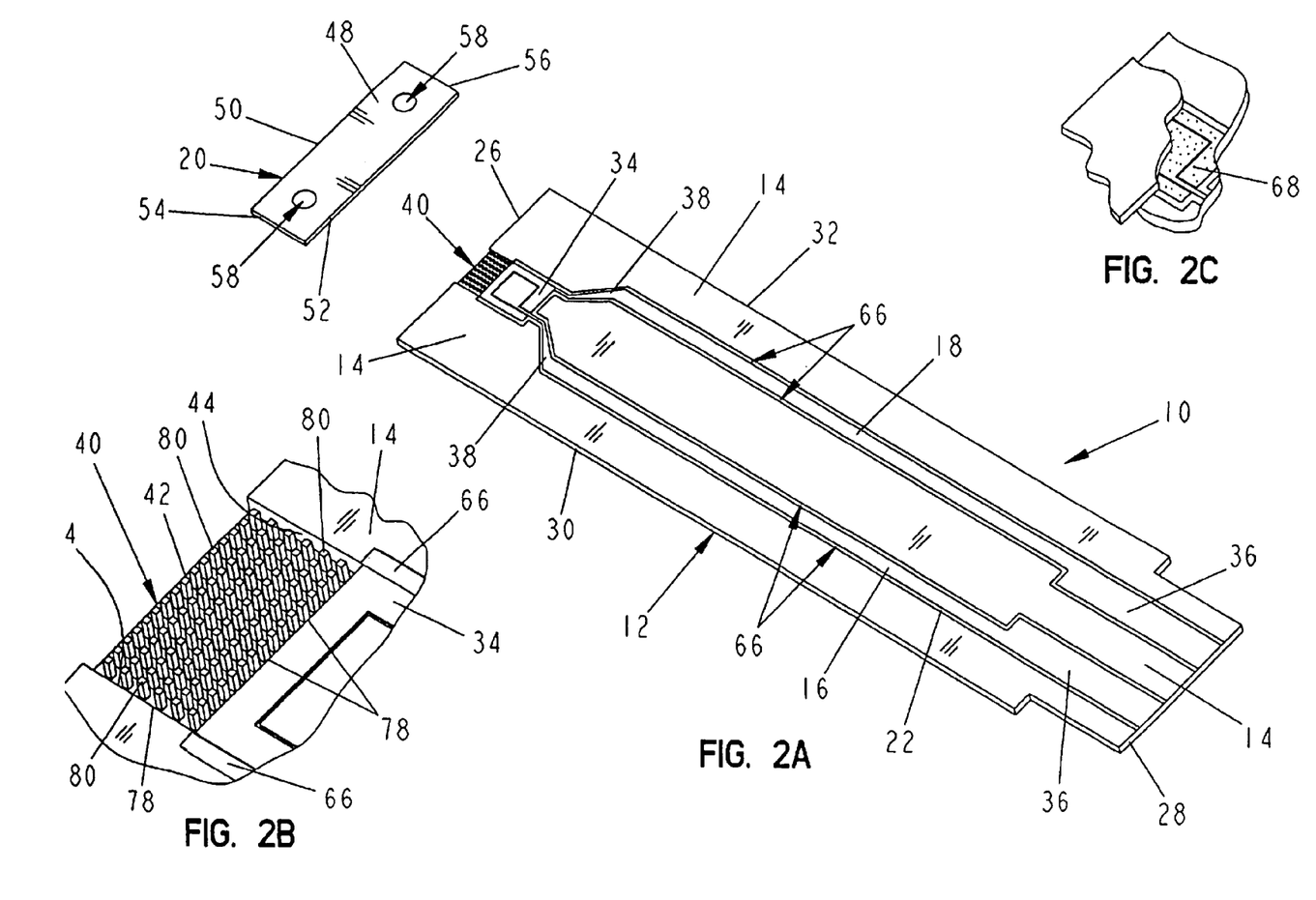
FIG. 2A is an exploded perspective view of the biosensor of FIG. 1.
FIG. 2B is an enlarged view of the biosensor of FIG. 2A showing the biosensor including a recess with a plurality of microstructures extending from a first surface of an electrode support substrate.
FIG. 2C is an enlarged view of the biosensor of FIG. 1 with portions broken away showing a reagent positioned on an electrode array.

As shown in FIG. 2A, electrodes 16, 18 cooperate with one another to define an electrode array 34. In addition, electrodes 16, 18 each include a contact 36 and a lead 38 extending between the contact 34 and the array 36. It is appreciated that the leads 38 extending from the array 34 can be formed to have many lengths and extend to a variety of locations on the electrode-support substrate 12. It is appreciated that the configuration of the electrode array, the number of electrodes, as well as the spacing between the electrodes may vary in accordance with this disclosure and that a greater than one array may be formed as will be appreciated by one of skill in the art Referring now to FIGS. 2A and 2B, a recess 40 is formed through the electrical conductor 14 and a portion of the first surface 22 of the support substrate 12 by laser ablation using techniques as described above. The recess 40 extends from end 26 of the substrate 12 to the electrode array 34. The recess 40 is defined further by walls 44. See FIG. 2B. It is appreciated that the amount of the support substrate 12 that is removed can vary in accordance with the present disclosure. It is also appreciated that substrate 12 of biosensor 10 can be formed without a recess in accordance with the present disclosure.

As best shown in FIG. 2B, the recess 40 includes a plurality of microstructures 42 extending from the first surface 22 of the support substrate 12. The microstructures 42 are spaced-apart from one another, on a nearest neighbor basis, by a fist distance that is less than the distance necessary to achieve capillary flow of liquid between the microstructures. Microstructures 42 are formed as posts that extend away from the substrate through the recess 40. See FIG. 3. Each microstructure 42 includes a fixed end 78 coupled to the substrate 12 and an opposite free end 80. Free end 80 exposed in channel 40 is metallic-coated. The substrate 12 is also cleaned, removing polymeric debris and other organic material and increasing the surface energy of surfaces of both the surface of the channel 40 and the microstructures 42.

It is appreciated that the microstructures 42 can assume a variety of shapes and sizes in accordance with the present disclosure. Illustratively, the recess 40 includes six rows of sixteen microstructures 42. The number and location of microstructures 42 depend upon the size of biosensor 10. The recess 40 may in fact be formed without microstructures in accordance with the present disclosure. In addition, it is also appreciated that the microstructures 42 may be positioned in a variety of locations in the recess 40. Although not shown, at least some of the microstructures can be joined to the walls 44 (FIG. 1) of the recess 40.

The cover substrate 20 is coupled to the electrode-support substrate 12 adjacent to the first end 26. See FIG. 1. The cover substrate 20 of biosensor 10 includes a first surface 46 facing substrate 12 and an opposite second surface 48. See FIG. 3. In addition, cover substrate 20 has opposite first and second ends 50, 52 and edges 54, 56 extending between ends 50, 52. Openings 58 extend between first and second surfaces 46, 48 and through any material coating either surface 46, 48. When cover substrate 20 is coupled to the support substrate 12, openings 58 are offset from array 34. See, FIG. 1. It is appreciated, however, that any number of openings 58 can be located in a number of locations and take on a variety of shapes and sizes in accordance with this disclosure.

Figure 3:
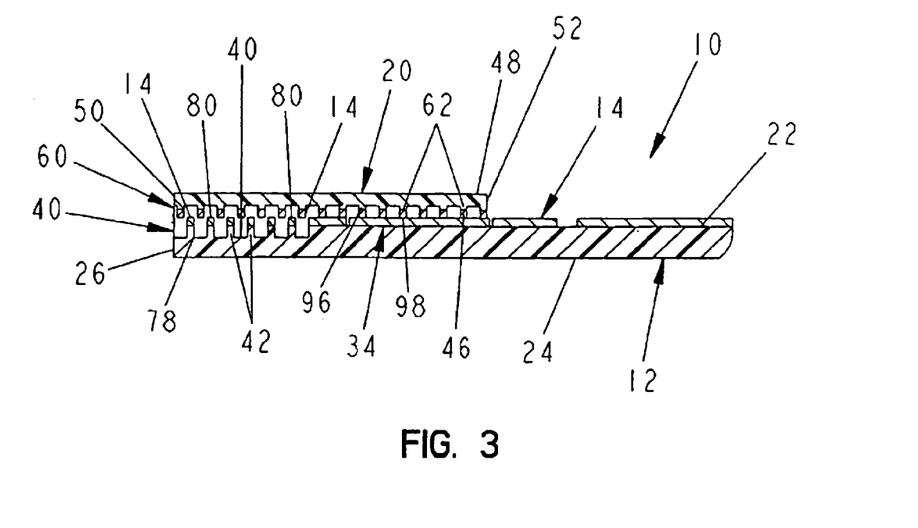
FIG. 3 is a view taken along lines 3—3 of FIG. 1.
Figure 4:
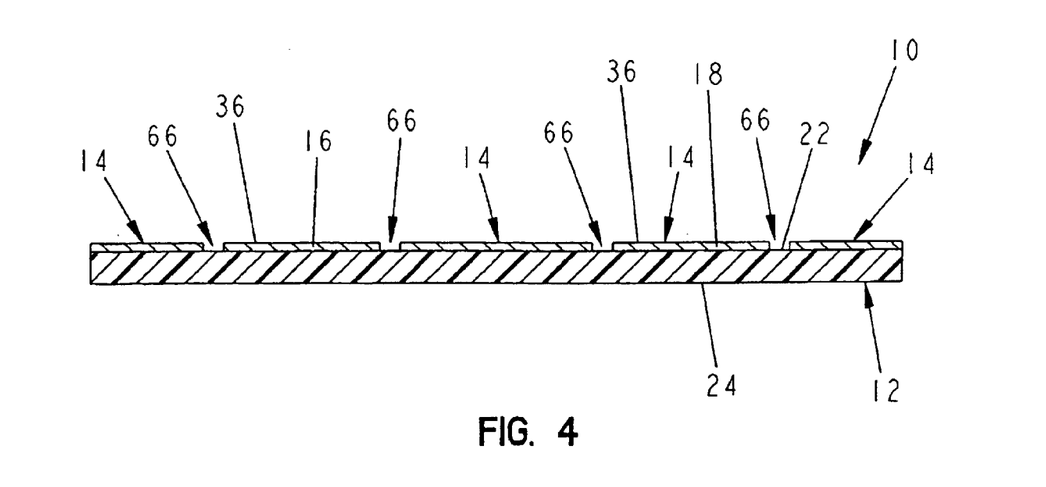
FIG. 4 is a view taken along lines 4—4 of FIG. 1.

The cover substrate 20 is formed of a flexible polymer and preferably from a polymer such as polyester. Referring now to FIG. 3, in preferred embodiments, the first surface 46 of the cover substrate 20 is coated with a metallic material 88 and preferably with a metal such as gold, platinum, palladium, and iridium. Preferably, the cover substrate 20 is 3 mil (75 um) Clear PEN film named KALADEX by DuPont and gold coated by: ROWO Coatings, Herbolzheim, Germany.

Figure 5:
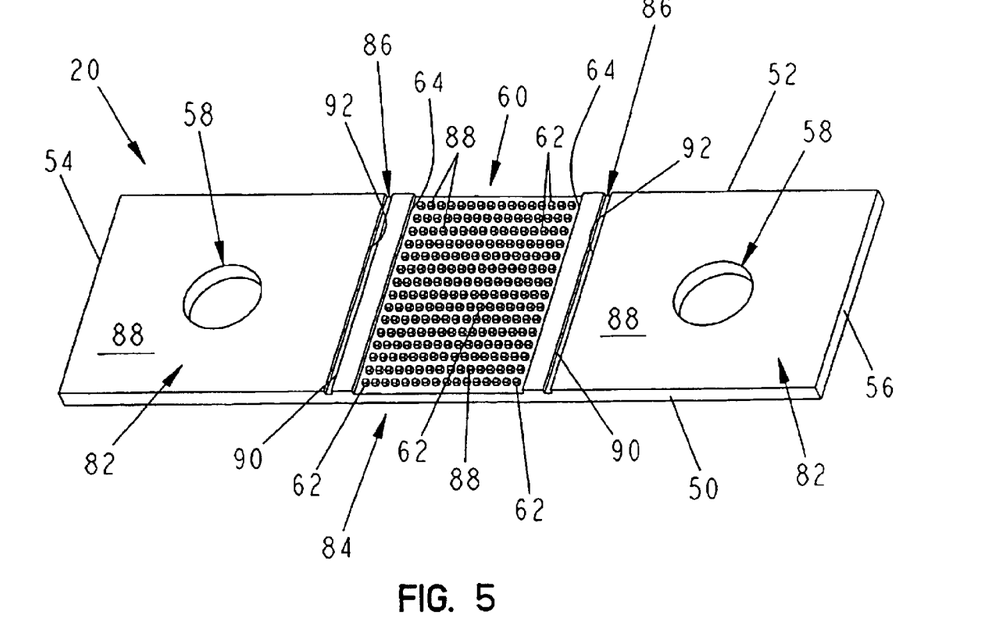
FIG. 5 is a bottom perspective view of a cover in accordance with one aspect of the invention showing the cover including a channel and plurality of square-shaped posts formed in the channel.

The cover substrate 20 is formed to include a capillary channel 60 and secondary capillary recesses 86 spaced-apart from channel 60. See FIG. 5. The capillary channel 60 is formed to provide a well-controlled fluid flow and simultaneously reduce the volume of liquid required in biosensor 10. As shown in FIG. 5, the capillary channel 60 extends between first and second ends 50, 52 and is defined by interior borders 64. The secondary capillary recesses 86 also extend between first and second ends 50, 52 and are defined by inner and outer borders 90, 92. The capillary channel 60 and secondary capillary recesses 86 are formed through at least the material 88 and preferably through a portion of the first surface 46 (FIG. 3) of the cover substrate 20 by laser ablation using techniques as described above. It is appreciated that the amount of the cover substrate 20 that is removed can vary in accordance with the present disclosure.

As shown in FIG. 5, the capillary channel 60 includes a plurality of microstructures 62. The microstructures 62 are spaced-apart from one another, on a nearest neighbor basis, by a first distance that is less than the distance necessary to achieve capillary flow of liquid between the microstructures. The capillary channel 60 illustrated in FIG. 5 includes sixteen rows of sixteen microstructures 62. The number and location of microstructures 62 depend upon the size of biosensor. Microstructures 62 shown in FIG. 5 are formed as generally square-shaped posts. It is appreciated, however, that microstructures can have a variety of shapes and sizes, non-limiting examples of which are illustrated in FIGS. 6–8 and 11, in accordance with this disclosure.

Microstructures 62 extend away from the cover substrate 20 into the capillary channel. See FIG. 5. Each microstructure 62 includes a fixed end 96 coupled to the cover substrate 20 and an opposite free end 98. The cover substrate 20 is also cleaned, removing polymeric debris and other organic material present and increasing the surface energy of surfaces of both the surface of the channel 60 and the microstructures 42. It is also appreciated that the microstructures 62 may be positioned in a variety of locations in the channel 60 as discussed above with reference to microstructures 42.

Once the cover substrate 20 is coupled to the support substrate 12, the channel 60 is aligned with recess 40. Channel 60 has a height of about 1 $\mu$m to about 60 $\mu$m, preferably 2 $\mu$m to about 30 $\mu$m, and most preferably about 51 $\mu$m to about 15 $\mu$m. In addition, the width of channel 60 between interior borders 64 is about 1 mm to about 4 mm, preferably 1.5 mm to about 3.0 mm, most preferably about 2.0 mm to about 2.5 mm. The channel 60 and the recess 40 cooperate to define a capillary path. It is appreciated that when the substrate 12 does not include the recess 40, the channel 60 itself will define the capillary path. Moreover, it is appreciated that while the capillary path is illustratively straight, the capillary path may be curved and/or include turns.

The cover substrate 20 is coupled to the electrode-support substrate 12 with an adhesive to create sealed portions 82 spaced-apart from the array 34 and an unsealed portion 84 extending between ends 50, 52 and across at least a portion of the array 34. See FIGS. 1 and 5. Referring now to FIG. 5, each sealed portion 82 has an interior border that lies in general alignment with secondary capillary recesses 86 and an exterior border. The exterior border of each sealed portion 82 lies in general alignment with a respective edge 54, 56 of the electrode-support substrate 12. Although the sealed portions 82 are not distinguishable to the user, it is appreciated that the cover substrate 20 can be at least partially transparent, exposing the recess 40 to the user when a colored fluid such as blood flows it. In addition, it is appreciated that the shape and size of the cover substrate 20 can vary in accordance with this disclosure.

The cover substrate 20 is coupled to the support substrate 12 by a liquid adhesive. A non-limiting example of such an adhesive is EPO-TEK OH100-4 commercially available from Epoxy Technology, Billerica, Mass. Preferably, a heated tool is applied on the area where bonding is to take place to promote fast curing. It is appreciated that the cover substrate 20 may be coupled to the support substrate 12 using a wide variety of commercially available adhesives as well as heat sealing, or ultrasonic methods of joining the cover substrate 20 and support substrate 12 together in accordance with this disclosure.

Referring now to FIG. 2C, a reagent 68 is positioned on the array 36. When the biosensor is an electrochemical biosensor, the reagent 68 provides electrochemical probes for specific analytes. It is appreciated, however, that reagent 68 can also be formed for use in a photometric biosensor. When, however, biosensor is a photometric biosensor, other aspects of the biosensor construction will change to accommodate photometric measurements. Such a construction is well known in the art. The choice of the specific reagent 68 depends on the specific analyte or analytes to be measured, and are well known to those of ordinary skill in the art An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100–900 kilo Daltons), 3.3 mg NATROSOL 244M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is expressly incorporated herein by reference.

Non-limiting examples of enzymes and mediators that may be used in measuring particular analytes in biosensor 10 are listed below in Table 1.

TABLE 1

| Analyte | Enzymes | Mediator (Oxidized Form) | Additional Mediator |
| --- | --- | --- | --- |
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |

TABLE 1-continued

| Analyte | Enzymes | Mediator (Oxidized Form) | Additional Mediator |
|---|---|---|---|
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensor 10 in accordance with this disclosure.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in a cassette magazine, or packed in blister packaging.

Biosensor 10 is used in conjunction with the following:
1. a power source in electrical connection with contacts 36 and capable of supplying an electrical potential difference between electrodes 16, 18 sufficient to cause diffusion limited electro-oxidation of the reduced form of the mediator at the surface of the working electrode; and
2. a meter in electrical connection with contacts 36 and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of each of which are expressly hereby incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, whole blood is assayed with this invention.

Figure 9:
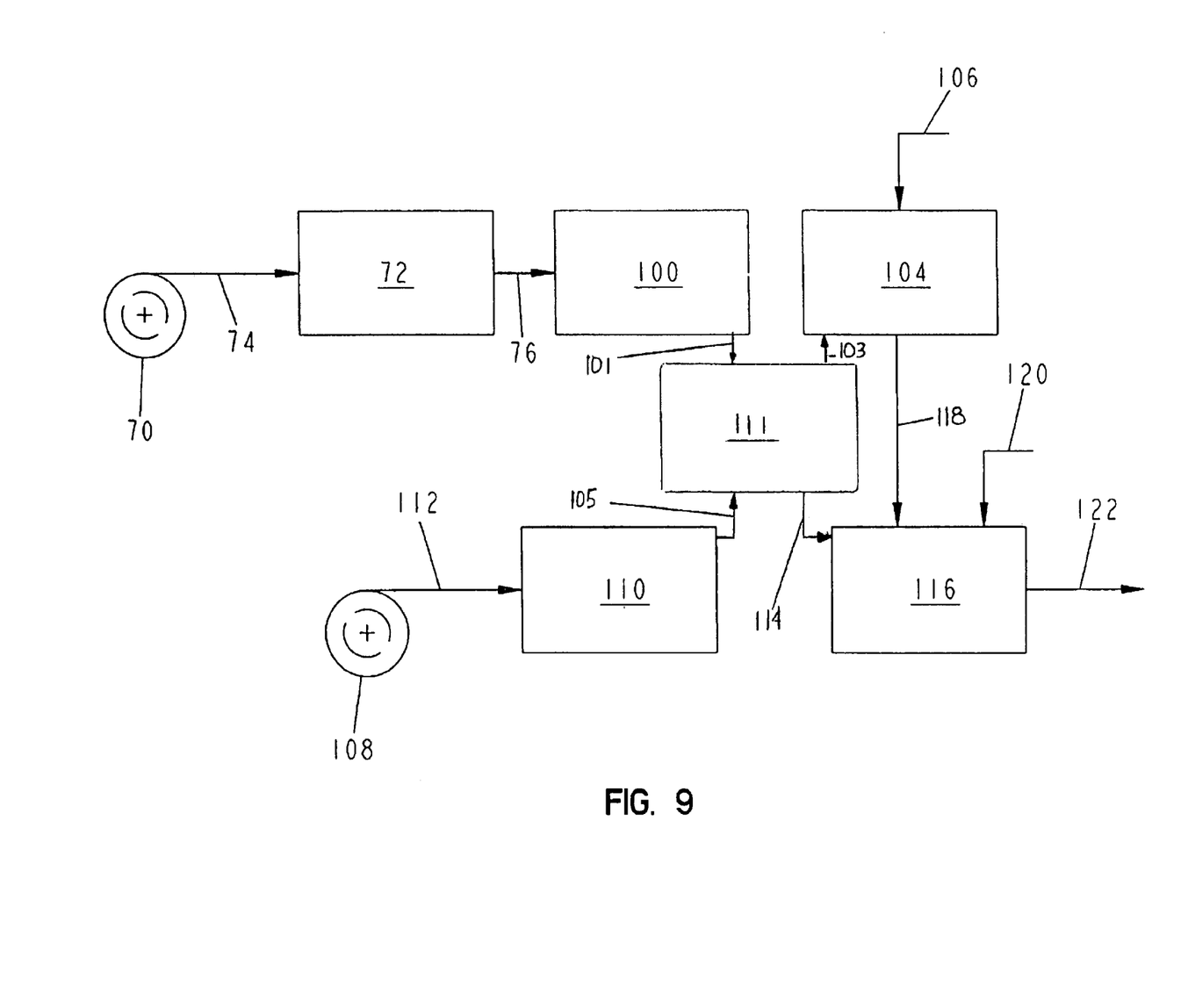
FIG. 9 is a diagrammatic view of a manufacturing method in accordance with the present invention.

As shown in FIG. 9, biosensor 10 is manufactured by feeding a roll of metallized electrode support material through guide rolls 70 into a first ablation station 72 as shown by arrow 74. A laser system capable of ablating support 12 is known to those of ordinary skill in the art. Non-limiting examples of which include excimer lasers, with the pattern of ablation controlled by mirrors, lenses, and masks. A non-limiting example of such a custom fit system is the LPX-300 or LPX-200 both commercially available from LPKF Laser Electronic GmbH, of Garbsen, Germany, equipped with a 248 nm wavelength excimer laser. It is appreciated that higher wavelength UV lasers can, however, be used in accordance with this disclosure.

In the first laser ablation station 72, the metallic layer of the metallized film is ablated in a predetermined pattern, to form a ribbon of isolated electrode sets on the electrode support material. To ablate electrodes 16, 18 isolated by gaps 66 in 50 nm thick gold conductor 14, 90 mJ/cm$^2$ energy is applied. It is appreciated, however, that the amount of energy required may vary from material to material, metal to metal, or thickness to thickness. The ribbon is then passed through more guide rolls, with a tension loop and through an optional inspection system where both optical and electrical inspection can be made. The system is used for quality control in order to check for defects.

Next, the ribbon is fed, as shown by arrow 76 into a second laser ablation station 100. Station 100 is similar to station 72. In the second station 100, the first surface 22 of the support substrate 12 is ablated in a predetermined pattern, to form the recess 40 extending about the microstructures 42. To ablate the recess 40 in 50 nm thick gold conductor 14 and 4 micrometers into the surface 22, multi-pulses of the laser light are applied. In preferred embodiments, three to five pulses of laser light (90 mJ/cm$^2$ in each pulse) are applied. It is appreciated the depth of ablation into the surface 22 can vary. Moreover, it is appreciated that the number of pulses applied will very depending upon the polymer and the depth of ablation. For example, as the hardness of the polymer increases the number of pulses will increase (a non-limiting example of which is 25 pulses) and as the hardness of polymer decreases, the number of pulses necessary to ablate the surface 22 decreases. If any seed layer or other metallic layer such as Chromium or Titanium or any other metal is used for any purpose, and then gold is put down on top of the seed layer or other metallic layer, the total thickness of all composite metals is still preferred to be 50 nm. It is appreciated, however, if the total thickness is higher, a higher energy laser will be needed.

Upon leaving the second laser ablation station 100, the ablated material that is in either roll form or that has been cut into cards is fed as shown by arrow 101 to a microwave plasma machine 111, a custom-fit equipment, which is commercially available from TePla AG, Kircheim, Germany. The ablated material is cleaned by the microwave plasma machine to remove polymeric debris and other organic material and to increase the hydrophilicity of the channel 40 and microstructures 42. Non-limiting parameters of a plasma machine are as follows: pressure=0.44 mbar: gas=Oxygen; Microwave power=300 watt; time=about 30 to about 60 seconds. Cleaning with the microwave plasma machine results in increased surface energy as well as the removal or loose particles, making the surfaces very hydrophilic, which helps increase the blood flow rate and fluid spreading. For example, the surface energy of recess 42 as well as the surface 14 before treatment with the plasma machine ≅41 mN/m. The surface energy after the treatment ≅72 mN/m.

Upon leaving the microwave plasma machine 111, the metallized film is fed as shown by arrow 103 into a reagent dispensing station 104. Reagents that have been compounded are fed, as shown by arrow 106, into the dispensing station 104 where it is applied in a liquid form in multiple shots to the array 34. It is appreciated, however, that the reagent can be applied by multi or single dose by a custom fit precision dispensing station available from Fluilogic Systems Oy, Espoo, Finland. Reagent application techniques are well known to one of ordinary skill in the art as described in U.S. Pat. No. 5,762,770, the disclosure of which is expressly incorporated herein by reference. It is appreciated that reagents may be applied to the array 34 in a liquid or other form and dried or semi-dried onto the array 34 in accordance with this disclosure.

In a separate process, a roll of metallized film through guide rolls 108 into a third ablation station 10 as shown by arrow 112. The station 10 is similar to station 72. It is appreciated that although three laser ablation stations are illustrated and described, that greater or fewer than three stations may be used in accordance with the disclosure. In the third station 10, the metallized film and first surface 46 of the material is ablated in a predetermined pattern, to form the capillary channel 60 extending about microstructures 62 and secondary capillary recesses 86. To ablate channel 60 and recesses 86 in 50 nm thick gold conductor 14 and 4 micrometers into the surface 46, multi-pulses of the laser light are applied. In preferred embodiments, three to five pulses of laser light (90 MJ/cm$^2$ in each pulse) are applied. It is appreciated the depth of ablation into the surface 46 can vary. Moreover, it is appreciated that the number of pulses applied will very depending upon the polymer and the depth of ablation. For example, as the hardness of the polymer increases the number of pulses will increase (a non-limiting example of which is 25 pulses) and as the hardness of polymer decreases, the number of pulses necessary to ablate the surface 46 decreases. If any seed layer or other metallic layer such as Chromium or Titanium or any other metal is used for any purpose, and then gold is put down on top of the seed layer or other metallic layer, the total thickness of all composite metals is still preferred to be 50 nm. It is appreciated, however, if the total thickness is higher, a higher energy laser will be needed.

Upon leaving the third laser ablation station 110, the ablated material that is in either roll form or that has been cut into cards is fed as shown by arrow 105 to the microwave plasma machine 111. It is appreciated, however, that a second plasma machine could also be used in accordance with this invention. Cleaning with the plasma machine 111 results in the removal of polymeric debris and other organic materials and increased surface energy, making the surfaces very hydrophilic, which helps increase the blood flow rate and fluid spreading. For example, the surface energy of the capillary channel 60 as well as the surface 46 before treatment with the plasma machine ≅41 mN/m. The surface energy after the treatment ≅72 mN/m.

Upon leaving the microwave plasma machine 111, the film is then fed as shown by arrow 114 into a sensor lamination and cut/pack station 116. At the same time, the reagent-coated film is fed, as shown by arrow 118 into the station 116. The cover support material is punched to form openings 58. The first surface 46 of the cover support material is then applied to the electrode-support substrate material over the electrode arrays 34. Next, a liquid adhesive is dispensed, as shown by arrow 120 through openings 58 of the cover substrate material in the station 116. A heated tool is applied on the area where bonding is to take place to promote fast curing of the adhesive between isolated gold surfaces 46 and 14.

The resulting assembled material is cut to form individual biosensors 10, which are sorted and packed into vials, each closed with a stopper, to give packaged, biosensor strips as shown by arrow 122.

In use, for example, a user of biosensor 10 places a finger having a blood collection incision against ends 26, 50 adjacent to openings of recess 40 and channel 60. See, FIG. 3. Capillary forces pull a liquid sample flowing from the incision through the capillary channel 60 across the reagent 68 and the array 36. The liquid sample dissolves the reagent 68 and engages the array 36 where the electrochemical reaction takes place.

The user then inserts the biosensor 10 into a meter (not shown) where an electrical connection is made between the electrode contacts 36 and a meter contact (not shown) in the meter. It is appreciated that the biosensor 10 also may be inserted into the meter at any number of times including prior to the sample flowing into the opening channel 60. Once the reaction is complete, a power source (e.g., a battery) applies a potential difference between the electrodes 16, 18. When the potential difference is applied, the amount of oxidized form of the mediator at the reference electrode and the potential difference must be sufficient to cause diffusion-limited electro-oxidation of the reduced form of the mediator at the surface of the working electrode. The current measuring meter (not shown) measures the diffusion-limited current generated by the oxidation of the reduced form of the mediator at the surface of the working electrode as described above.

The measured current may be accurately correlated to the concentration of the analyte in sample when the following requirements are satisfied:

1. The rate of oxidation of the reduced form of the mediator is governed by the rate of diffusion of the reduced form of the mediator to the surface of the working electrode.

2. The current produced is limited by the oxidation of reduced form of the mediator at the surface of the working electrode.

Figure 6:
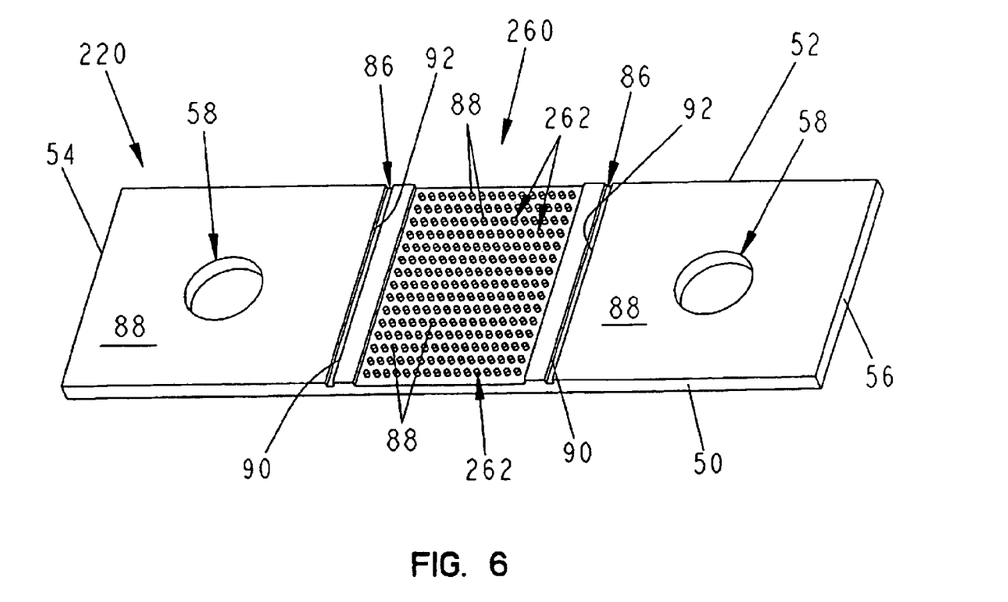
FIG. 6 is a bottom perspective view of a cover in accordance with another aspect of the invention showing the cover including a channel and plurality of round posts formed in the channel.

In another aspect of the invention, a cover substrate 220 is provided in accordance with the present disclosure. Cover substrate 220 is shown in FIG. 6 and is suitable for use with the electrode-support substrate 12. The cover substrate 220 is coupled to the electrode-support substrate 12 adjacent to the first end 26. The cover substrate 220 is formed of a flexible polymer coated with a metallic material similar to cover substrate 20.

The cover substrate 220 is formed to include a capillary channel 260 and secondary capillary recesses 86 spaced-apart from channel 260. Like channel 60 in cover 20, the capillary channel 260 is also formed to provide a well controlled fluid flow and simultaneously reduce the volume of liquid required when it cooperates with support substrate 12 in a biosensor. The capillary channel 260 and secondary capillary recesses 86 are formed through at least the material 88 and preferably through a portion of the first surface 46 of the cover substrate 220 by laser ablation using techniques as described above. It is appreciated that the amount of the cover substrate 220 that is removed can vary in accordance with the present disclosure.

As shown in FIG. 6, the capillary channel 260 includes a plurality of microstructures 262. The microstructures 262 are spaced-apart from one another, on a nearest neighbor basis, by a first distance that is less than the distance necessary to achieve capillary flow of liquid between the microstructures. It is appreciated that the capillary channel 260 can include greater or fewer than the illustrated microstructures in accordance with this disclosure. Microstructures 262 are formed as generally round-shaped posts. It is appreciated, however, that microstructures can have a variety of shapes and sizes in accordance with this disclosure. In addition, the cover substrate 220 is also cleaned, as described above with reference to cover 20, increasing the surface energy of surfaces of both the surface of the channel 40 and the microstructures 42.

Figure 7:
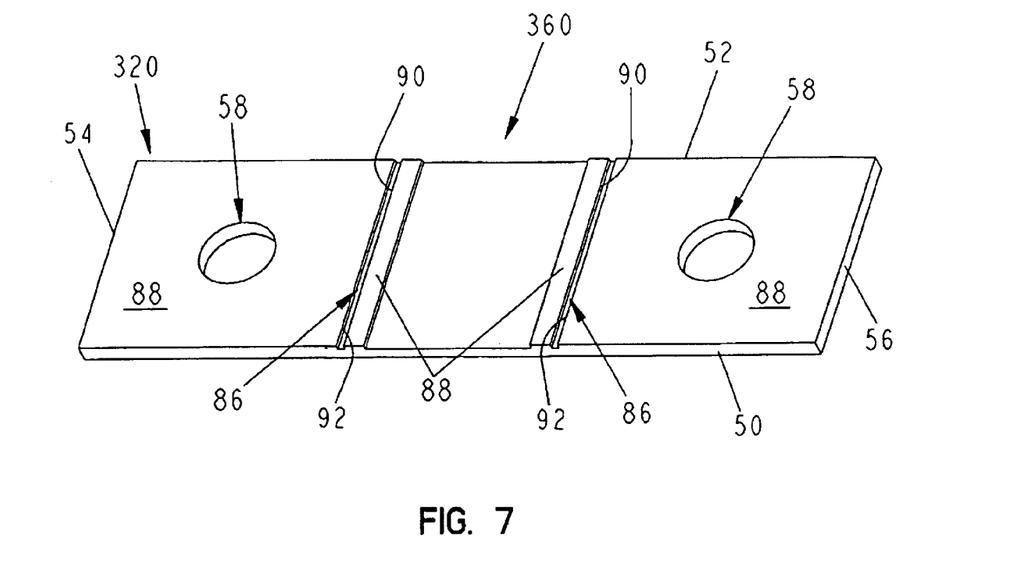
FIG. 7 is a bottom perspective view of a cover in accordance with another aspect of the invention showing the cover including a channel and two spaced-apart bar-shaped posts formed in the channel.

In another aspect of the invention, a cover substrate 320 is provided in accordance with the present disclosure. Cover substrate 320 is shown in FIG. 7 and is suitable for use with the electrode-support substrate 12. The cover substrate 320 is coupled to the electrode-support substrate 12 adjacent to the first end 26. The cover substrate 320 is formed of a flexible polymer coated with a metallic material similar to cover substrate 20.

The cover substrate 320 is formed to include a capillary channel 360 and secondary capillary recesses 86 spaced-apart from channel 360. Like channel 60 in cover 20, the capillary channel 360 is also formed to provide a well controlled fluid flow and simultaneously reduce the volume of liquid required when it cooperates with support substrate 12 in a biosensor. The capillary channel 360 and secondary capillary recesses 86 are formed through at least the material 88 and preferably through a portion of the first surface 46 of the cover substrate 320 by laser ablation using techniques as described above. It is appreciated that the amount of the cover substrate 320 that is removed can vary in accordance with the present disclosure. Further, the cover substrate 320 is also cleaned, as described above with reference to cover 20, increasing the surface energy of the surface of the channel 360.

Figure 8:
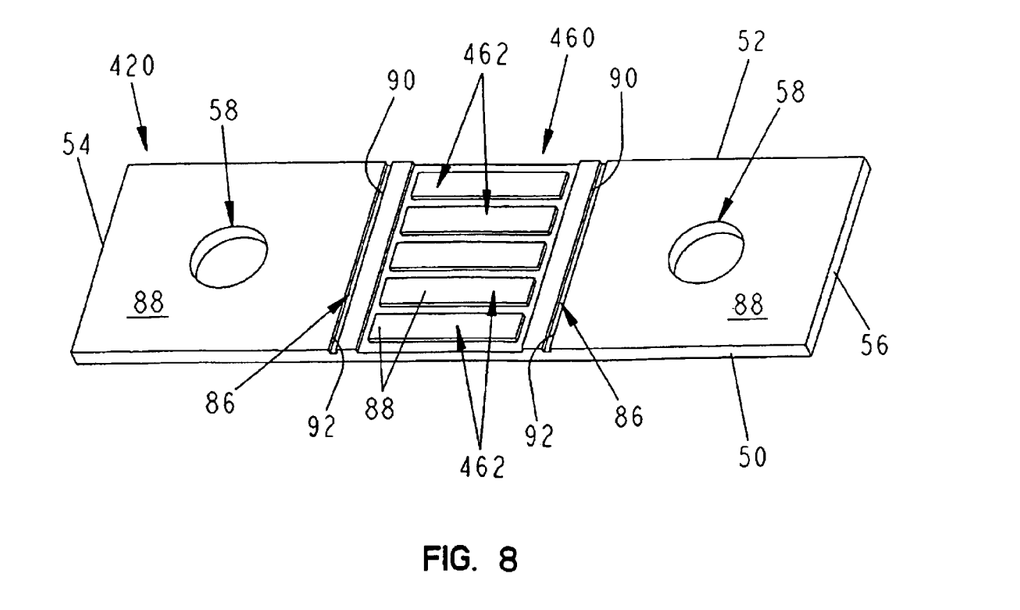
FIG. 8 is a bottom perspective view of a cover in accordance with another aspect of the invention showing the cover including a channel and plurality of bar-shaped posts formed in the channel.

In another aspect of the invention, a cover substrate 420 is provided in accordance with the present disclosure. Cover substrate 420 is shown in FIG. 8 and is suitable for use with the electrode-support substrate 12. The cover substrate 420 is coupled to the electrode-support substrate 12 adjacent to the first end 26. The cover substrate 420 is formed of a flexible polymer coated with a metallic material similar to cover substrate 20.

The cover substrate 420 is formed to include a capillary channel 460 and secondary capillary recesses 86 spaced-apart from channel 460. Like channel 60 in cover 20, the capillary channel 460 is also formed to provide a well controlled fluid flow and simultaneously reduce the volume of liquid required when it cooperates with support substrate 12 in a biosensor. The capillary channel 460 and secondary capillary recesses 86 are formed through at least the material 88 and preferably through a portion of the first surface 46 of the cover substrate 420 by laser ablation using techniques as described above. It is appreciated that the amount of the cover substrate 420 that is removed can vary in accordance with the present disclosure.

As shown in FIG. 8, the capillary channel 460 includes a plurality of microstructures 462. The microstructures 462 are spaced-apart from one another, on a nearest neighbor basis, by a first distance that is less than the distance necessary to achieve capillary flow of liquid between the microstructures. Illustratively, the capillary channel 460 includes five rows of microstructures 462. It is appreciated that the capillary channel 460 can include greater or fewer than the illustrated microstructures in accordance with this disclosure. Microstructures 462 are formed as generally bar-shaped posts. It is appreciated, however, that microstructures can have a variety of shapes and sizes in accordance with this disclosure. Further, the cover substrate 420 is also cleaned, as described above with reference to cover 20, a increasing the surface energy of surfaces of both the surface of the channel 460 and the microstructures 462.

Figure 10:
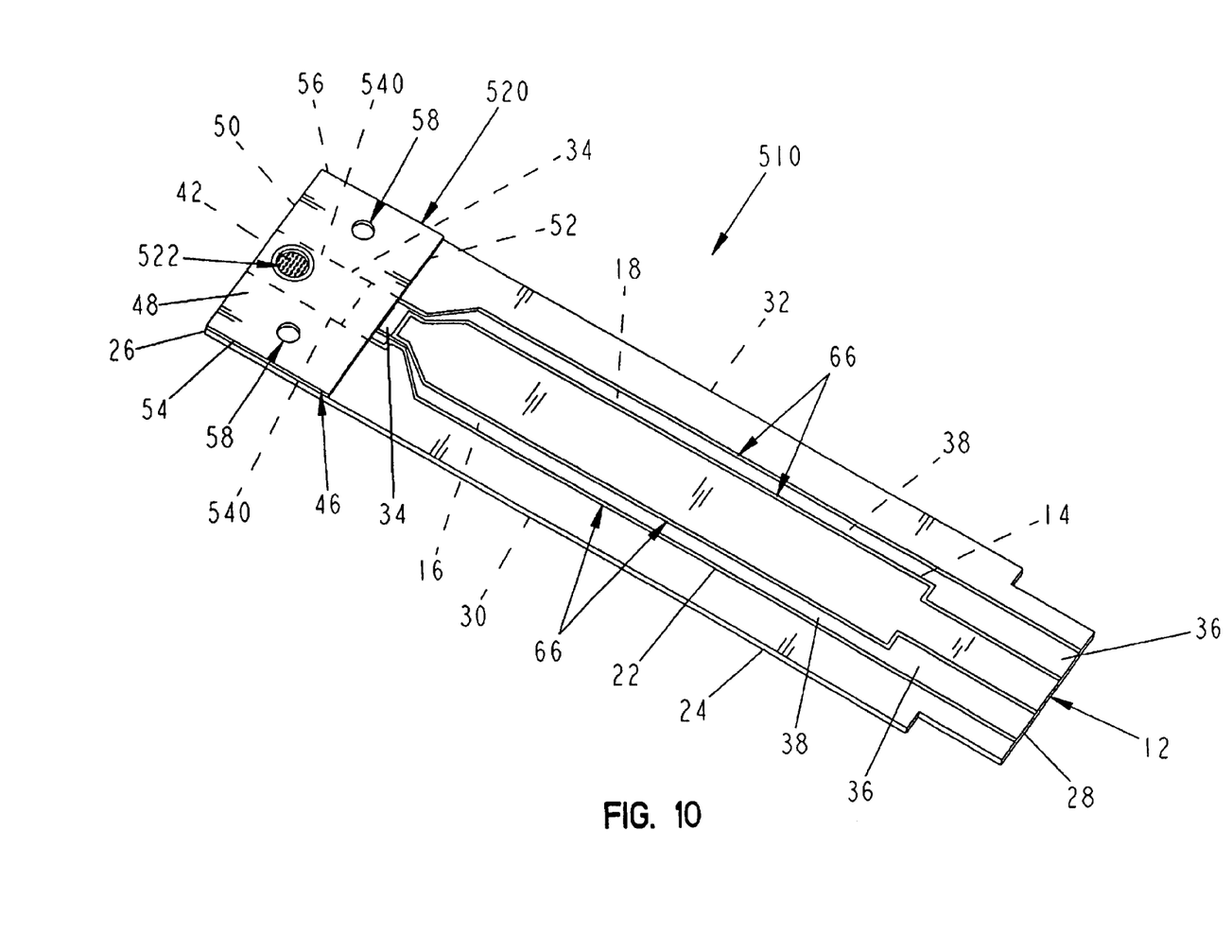
FIG. 10 is a perspective view of a biosensor in accordance with the present invention.

As shown in FIG. 10, biosensor 510 is formed to include an electrode-support substrate 512. Substrate 512 is formed in a similar manner to substrate 12, except that the electrode array 34 is spaced-apart from first end 26 and a recess 540 including microstructures 42 extends between end 26 and array 34. The recess is formed through the electrical conductor 14 and a portion of the first surface 22 of the support substrate 512 by laser ablation using techniques as described above. It is appreciated that the amount of the support substrate 512 that is removed can vary in accordance with the present disclosure. It is also appreciated that substrate 512 of biosensor 510 can be formed without a recess in accordance with the present disclosure. It is also appreciated that the microstructures 42 can assume a variety of shapes and sizes in accordance with the present disclosure.

Figure 11:
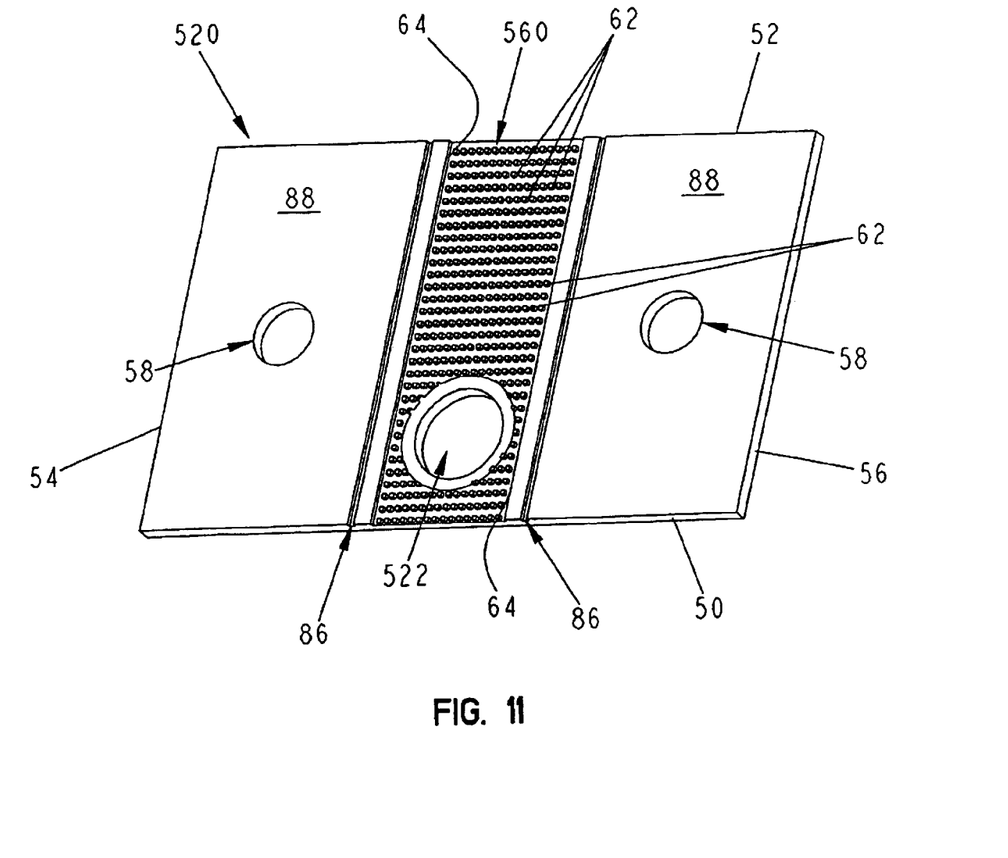
FIG. 11 is a bottom perspective view of the cover of the biosensor of FIG. 10.

The cover substrate 520 is coupled to the electrode-support substrate 12 adjacent to the first end 26. See FIG. 10. The cover substrate 520 is formed of materials similar to the cover substrate 20 as described above. Referring now to FIG. 11, the cover substrate 520 is formed to include a capillary channel 560 and secondary capillary recesses 86 spaced-apart from channel 560. The capillary channel 560 is formed to provide a well-controlled fluid flow and simultaneously reduce the volume of liquid required in biosensor 510. The capillary channel 560 extends between first and second ends 50, 52 and is defined by interior borders 64. The capillary channel 560 and secondary capillary recesses 86 are formed through at least the material 88 and preferably through a portion of the first surface of the cover substrate 20 by laser ablation using techniques as described above. It is appreciated that the amount of the cover substrate 520 that is removed can vary in accordance with the present invention.

As shown in FIG. 11, the capillary channel 560 includes microstructures 62 that are formed as described above with reference to biosensor 10. It is appreciated that the microstructures 62 can assume a variety of shapes and sizes the number and location of microstructures 62 depend upon the size of biosensor in accordance with the present disclosure.

In addition, the cover substrate 520 is formed to include an inlet 522 that extends between first and second surfaces 46, 48 in the capillary channel 560. When the cover substrate 520 is coupled to the support substrate 512, the inlet 522 is offset from the array 34. See, FIG. 10. It is appreciated, however, that inlet 522 can be located in a number of locations in the channel 560 in accordance with this disclosure, a non-limiting example of which includes the inlet 522 intersecting end 50 of cover substrate 520.

Biosensor 510 is manufactured in a manner similar to biosensor 10 as described above. Recess 540 of the biosensor 510 is formed in the second laser ablation station 100 by ablating the first surface 22 in a pre-defined pattern to form the recess 540 extending between end 26 and the array 36. The hydrophilicity of the channel 540 and microstructures 42 are increased due to cleaning by a plasma machine 111 as described above with reference to biosensor 10. Capillary channel 560 is formed in the cover substrate material in the third ablation station 110 as described above with reference to biosensor 10. The ablated material is cleaned by the plasma machine 111 to remove polymeric debris and other organic materials and increasing the hydrophilicity of the channel 560 and microstructures 62. The film is then fed into the sensor lamination and cut/pack station 116 where openings 58 and inlet 522 are punched.

As described above with reference to biosensor 10, a liquid adhesive is dispensed, through openings 58 of the cover substrate material and a heated tool is applied on the area where bonding is to take place to promote fast curing of the adhesive. The resulting assembled material is cut to form individual biosensors 510, which are sorted and packed into vials, each closed with a stopper, to give packaged biosensor strips. The biosensor 510 is used in a manner similar to biosensor 10 as described above.

Although the invention has been described in detail with reference to a preferred embodiment, variations and modifications exist within the scope and spirit of the invention, on as described and defined in the following claims.

What is claimed is:

1. A biosensor comprising:
   a substrate,
   a cover extending across at least a portion of the substrate, the cover including a first surface facing the substrate and a second surface, a capillary channel being defined in at least a portion of the first surface, the capillary channel having a surface energy ranging from about 60 mN/m to about 72 mN/m, and
   at least one microstructure including a fixed end coupled to either the substrate or the cover and an opposite free end exposed in the capillary channel, wherein the free end of each microstructure has an exposed metallic coating.

2. The biosensor of claim 1 wherein the first surface is formed to include the at least one microstructure extending into the channel.

3. The biosensor of claim 2 wherein at least one of the microstructures has a round post-like shape.

4. The biosensor of claim 2 wherein at least one of the microstructures has a generally square post-like shape.

5. The biosensor of claim 2 wherein the capillary channel includes opposite ends and the first surface is formed to include at least two microstructures that include a front side facing one end and a back side facing the opposite end and opposite inner and outer edges that extend between the front and back sides.

6. The biosensor of claim 5 wherein the front side and the back side of the at least two microstructures each have a greater dimension than the inner and outer edges.

7. The biosensor of claim 6 wherein the metallic coating is gold.

8. The biosensor of claim 1 wherein the first surface includes spaced-apart secondary capillary recesses.

9. The biosensor of claim 1 wherein at least a portion of the first surface includes a metallic coating.

10. A biosensor comprising:
    a capillary path defined between a substrate and a cover, the path having a surface energy ranging from about 60 mN/m to about 72 mN/m,
    electrodes positioned on the substrate, and
    at least one microstructure positioned in the capillary path, the at least one microstructure including a fixed end coupled to either the substrate or the cover and an opposite free end, wherein the free end of each microstructure has an exposed metallic coating.

11. The biosensor of claim 10 wherein the capillary path has a surface energy ranging from about 60 mN/m to about 72 mN/m.

12. The biosensor of claim 10 wherein the free end is coated with a metal selected from the group consisting of gold, platinum, palladium, and iridium.

13. The biosensor of claim 12 wherein the metal is gold.

14. The biosensor of claim 10 wherein at least one of the microstructures has a round post-like shape.

15. The biosensor of claim 10 wherein at least one of the microstructures has a generally square post-like shape.

16. A biosensor comprising:
    a substrate,
    electrodes positioned on the substrate,
    a cover extending across at least a portion of the substrate to define a capillary path, and
    at least one microstructure positioned in the capillary path, the at least one microstructure including a fixed end coupled to the cover and an opposite free end, wherein the free end of each microstructure has an exposed metallic coating.

17. The biosensor of claim 16 wherein the free end formed of a metal selected from the group consisting of gold, platinum, palladium, and iridium.

18. The biosensor of claim 16 wherein the metal is gold.

19. The biosensor of claim 16 wherein the microstructures have a surface energy ranging from about 60 mN/m to about 72 mN/m.

20. A method of forming a biosensor, the method comprising the steps of:
    providing a substrate, a reagent for the measurement of at least one analyte, and a cover, the cover including a first surface,
    exposing the cover to at least one pulse of light ablating the first surface in a pre-determined pattern creating a channel, forming electrodes on the substrate, wherein the forming step includes exposing the substrate to at least one pulse of light sufficient to ablate a portion of the substrate about the electrodes;

cleaning the first surface of the cover so that the surface energy of the channel ranges from about 60 mN/m to about 72 mN/m, positioning the reagent upon the substrate, and placing the first surface of the cover upon the substrate to define a capillary path and the reagent is positioned in the capillary path.

21. The method of claim 20 wherein the first surface is cleaned by a microwave plasma machine.

22. The method of claim 20 wherein the first surface is ablated to create microstructures in the channel.

23. The method of claim 20 further comprising the step of exposing the substrate to at least an additional pulse of light sufficient to ablate a portion of the substrate creating at lest one microstructure extending from the substrate.

24. The method of claim 20 further comprising the step of cleaning the substrate to increase the surface energy of the substrate.

25. The method of claim 20 further comprising the steps of positioning a mask having a pre-defined pattern over the first surface and exposing the mask and the cover to at least one pulse of light sufficient to ablate the exposed surface of the cover creating at least one microstructure extending from the cover.

* * * * *